United States Patent [19]

Hawke et al.

[11] 4,279,164
[45] Jul. 21, 1981

[54] METALLURGICAL SPECIMEN TESTER

[75] Inventors: Merrill P. Hawke, Lytle; Pete Elizalde, Jr.; Robert L. Harris, both of San Antonio, all of Tex.

[73] Assignee: The United States of America as represented by the Secretary of the Air Force, Washington, D.C.

[21] Appl. No.: 115,843

[22] Filed: Jan. 28, 1980

[51] Int. Cl.³ .............................................. G01N 3/08
[52] U.S. Cl. ...................................................... 73/826
[58] Field of Search ............. 73/826, 828, 830, 141 R; 254/204

[56] References Cited

U.S. PATENT DOCUMENTS 2,709,233  5/1955  Hage .................................. 73/826 X
3,965,729  6/1976  King, Jr. .

Primary Examiner—Jerry W. Myracle
Attorney, Agent, or Firm—Donald J. Singer; Arsen Tashjian

[57] ABSTRACT

A plurality of cantilever beams, each fitted with a calibrated strain gage, are arranged to pivot on a corresponding plurality of upstanding pivots located near one end of each beam of a steel plate. A cylindrical specimen threaded at each end is disposed vertically between one end of each beam and the steel plate with a machined nut and socket at each end of the specimen to provide self-alignment. A self-aligning hardened steel stud is threaded into the plate and held in a hole in the other end of each of the beams with a nut and socket. A tension load is applied to the specimen by torquing the nut on the stud, with the mechanical advantage being proportional to the relative distances between the pivot and the specimen and the pivot and the stud.

5 Claims, 5 Drawing Figures

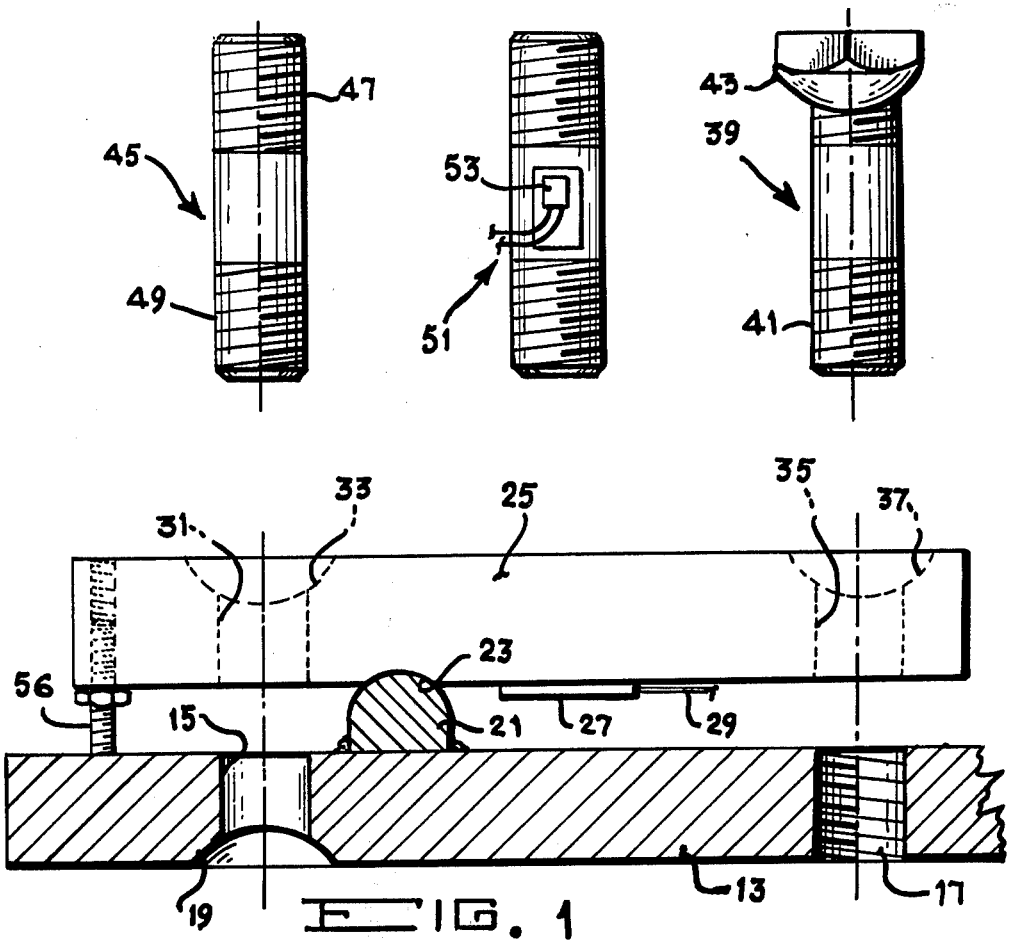
FIG. 3  FIG. 4  FIG. 2
FIG. 1
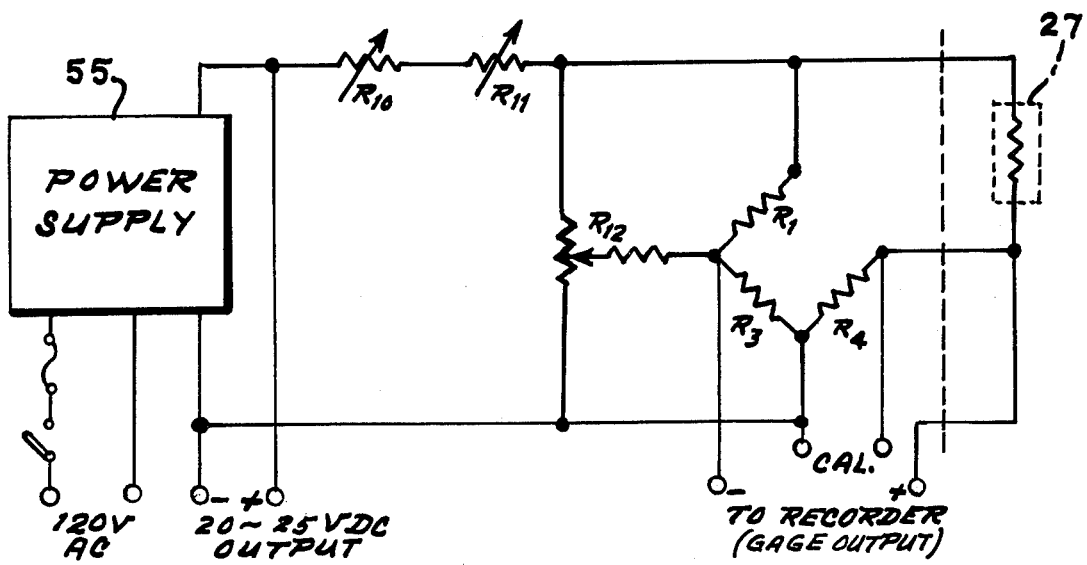
FIG. 5

METALLURGICAL SPECIMEN TESTER

STATEMENT OF GOVERNMENT INTEREST

The invention described herein may be manufactured and used by or for the Government for governmental purposes without the payment of any royalty thereon.

BACKGROUND OF THE INVENTION

This invention relates to testing a metallurgical specimen and, more particularly, the invention is concerned with providing an apparatus for testing a plurality of samples over a relatively long period of time while constantly monitoring and recording the results.

Various machines are available for testing specimens in tension, compression, torsion, etc. These machines generally apply stress to the test piece by moving parallel platforms either toward one another or, alternately, away from each other. This is accomplished by either mechanical screw arrangements or by hydraulic pressure. Although these machines are satisfactory for testing a single specimen to determine tensile and/or compression strength, they are not practical for testing a large number of specimens under load over a relatively long period of time. Many times it is desirable to determine the properties of a treated material by placing several specimens of the material under tension load for several days while at the same time, recording any changes that may occur in the material. Thus, it can be seen that there is a definite need for an apparatus which would be capable of testing ten or more samples accurately and simultaneously with constant monitoring by a recording system.

In the hereinafter disclosed invention, there is shown and described a testing apparatus which is capable of applying and maintaining a tension load on any large number of metallurgical specimens. For example, in the testing of metallurgical specimens, it may be necessary to certify that plating solutions and plated components are below the threshold of hydrogen embrittlement and that the heat treatment of components has lowered the level of diffused hydrogen to an acceptable level. Also, it may be necessary to correlate the quantity of diffused hydrogen and failure of specimens with the results obtained by means of a hydrogen determination analyzer. This can be accomplished by the use of the hereinafter described apparatus in a minimum of time and space as compared with other conventional and presently available testing arrangements.

SUMMARY OF THE INVENTION

The present invention is concerned with providing a metallurgical specimen tester for simultaneously loading, monitoring and recording a plurality of test samples in tension. The tester includes a steel plate with a plurality of upstanding pivots on which a corresponding plurality of cantilever beams with calibrated strain gages attached thereto, are arranged to pivot. Cylindrical specimens with convex nuts on each threaded end are positioned in aligned openings in one end of the beam and the steel plate. A hardened steel stud with a convex nut is positioned through an opening in the other end of the cantilever beam and threaded into the steel plate. The specimens are mechanically loaded up to 200,000 psi by torquing the nut on the hardened steel stud. The strain gage on the cantilever beam produces a signal which passes through a Wheatstone bridge circuit and is monitored and recorded on a conventional strip chart recorder.

Accordingly, it is an object of the invention to provide a metallurgical specimen tester which is capable of testing ten or more samples accurately and simultaneously with constant monitoring by a suitable recording system.

Another object of the invention is to provide a metallurgical specimen tester including a cantilever design that gives a mechanical advantage to permit loading of the specimen in excess of 200,000 psi by torquing a threaded hardened steel stud.

Still another object of the invention is to provide a metallurgical specimen tester which incorporates a self aligning feature by providing a plurality of convex nuts fitted to cavities in the mounting plate and cantilever beam on both ends of the specimen and on one end of a hardened steel stud in a cavity on the cantilever beam. This arrangement minimizes any possibility of axial bending in the specimen.

A further object of the invention is to provide a metallurgical specimen tester wherein a calibrated link having strain gages attached thereto is used to transfer calibration from a tensile machine to the specimen tester so that the actual applied load can be determined.

These and other objects, features and advantages will become more apparent after considering the following detailed description taken in conjunction with the annexed drawings and appended claims.

BRIEF DESCRIPTION OF THE DRAWINGS

FIG. 1 is a view in side elevation partially in section of the specimen tester according to the invention showing the cantilever beam in position with the specimen and load stud removed;

FIG. 2 is a side view of the load stud with the convex nut in position thereon;

FIG. 3 is a side view of a test specimen with the convex nuts removed;

FIG. 4 is a side view of a calibration link which is used in place of the specimen to calibrate the test apparatus; and FIG. 5 is a schematic diagram of the electrical circuitry showing the Wheatstone bridge circuit used with the strain gage to produce the signal for measuring the force being applied to the specimen.

DESCRIPTION OF A PREFERRED EMBODIMENT

Referring now to the drawings, in FIG. 1, there is shown a metallurgical specimen tester according to the invention including a steel plate 13 shown in section with a clearance hole 15 at one side thereof. A threaded hole 17 is located on the other side of the plate 13 in line with the hole 15. A concave cavity 19 is machined in the lower surface of the plate 13 on center with the hole 15. The steel plate 13 can be any convenient shape such as rectangular or circular and any size which would hold the number of specimens to be tested. The steel plate 13 is provided with an upstanding pivot 21 on its upper surface near the hole 15. A rounded surface on the upper end of pivot 21 engages a groove 23 on the lower surface of the cantilever beam 25.

A calibrated strain gage 27 with the leads 29 is fitted to the lower surface of the cantilever beam 25 about midway along the length thereof. A clearance hole 13 is located near one end of the cantilever beam 25 in axial alignment with the hole 15 in the steel plate 13. Another concave cavity 33 is machined in the upper surface of the cantilever beam 25 on center with the hole 31. Another clearance hole 35 is located near the other end of the cantilever beam 25 in axial alignment with the threaded hole 17. A third concave cavity 37 is machined on center with the hole 35.

In FIG. 2, there is shown a loading stud 39 with the lower end 41 threaded for engagement with the threads in the hole 17. A convex nut 43 is shown threadably attached to the upper end of the stud 39 for engagement with the concave cavity 37 in the upper surface of the cantilever beam 25. As the convex nut 43 is tightened when the stud 39 is in position on the tester, the cantilever beam 25 is caused to pivot and a load is applied to the specimen 45, shown in FIG. 3.

The specimen 45 is threaded on both ends so that a pair of convex nuts of the type shown on the stud 39 in FIG. 2 can be threadably attached to the specimen 45. The upper nut on the threads 47 of the specimen 45 would engage the concave cavity 33 on the upper surface of the cantilever beam 25 and the lower nut on the threads 49 of the specimen 45 would engage the concave cavity 19 on the lower surface of the steel plate 13 when the specimen 45 is in position on the tester.

In FIG. 4, there is shown a calibration link 51 upon which a pair of strain gages 53 (only one of which is shown) are mounted diametrically opposite each other. The calibration link 51 which is the same dimensions as the specimen 45, is calibrated on a tensile machine and then transferred to the specimen tester so that the readings indicated by the strain gage 27 can be correlated with the recorder to read stress on the specimen 45.

In FIG. 5, there is shown a schematic diagram of a typical Wheatstone bridge circuit used to monitor the output of the strain gage 27. A power source 55 supplies current through the bridge circuit paths $R_1$-$R_3$ and strain gage 27-$R_4$. As stress is applied to the cantilever beam 25, the resistance of the gage 27 changes in a corresponding amount. This unbalances the bridge thereby producing a difference in the voltage between the arms of the bridge. The resistors $R_{10}$ and $R_{11}$ are coarse and fine current adjustments, respectively, for the bridge circuit and the adjustable resistor $R_{12}$ is used to balance the bridge to zero. The output from the gage is connected to a suitable strip chart recorder (not shown) where the applied strain is monitored and recorded.

In operation, the metallurgical specimen tester is set up in the manner shown in FIG. 1 with the step 56 in position at the specimen end of the cantilever beam 25. The specimen 45 is then positioned in the holes 15 and 31 in the steel plate 13 and the cantilever beam 25, respectively. A convex nut like the one 43 shown in FIG. 2 is threadably attached to each end of the specimen 45 on the threads 47 and 49. The lower nut engages the concave cavity 19 in the lower surface of the steel plate 13 and the upper nut engages the concave cavity 33 in the upper surface of the cantilever beam 25. The convex nut and concave cavity arrangements form ball-and-socket type joints. The lower end of the hardened steel stud 39 is then threaded into the opening 17 in the steel plate 13 and the convex nut 43 is threadably attached to the upper end of the stud 39. A lubricant is placed on the convex nut 43 and threads of the stud 39.

As the convex nut 43 on the stud 39 is tightened, the specimen 45 is loaded in tension by the upward force on the specimen end of the cantilever beam 25. The strain gage 27 provides a signal proportional to the load applied to the cantilever beam 25. The signal is then used in the Wheatstone bridge circuit shown in FIG. 5, to feed a suitable recorder which provides a written record of the stress on the specimen 39. The calibration link 51 is used with a tensile machine to determine the impirical value of the tension load on the specimen 45 as it relates to the strain on the gage 27.

Although the invention has been illustrated in the foregoing specification in terms of a preferred embodiments thereof, the invention is not limited to these embodiments or to the particular configurations shown and described. It will be apparent to those skilled in the materials testing art that certain changes, modifications and substitutions can be made with respect to the shape of the elements without departing from the true spirit and scope of the appended claims. It can be seen that the hereinbefore described metallurgical specimen tests would be particularly useful as a tension creep-testing machine which normally involves the testing of a large number of samples for relatively long periods of time at various desired temperatures, above and below ambient.

Having thus set forth the nature of our invention, what we claim as new and desire to secure by Letters Patent of the United States is:

1. A metallurgical specimen tester for testing a plurality of like specimens in tension over a relatively long period of time, said specimen tester comprising a steel plate having at least two aligned spaced apart openings therein, one of said openings being threaded, an upstanding pivot positioned on the upper surface of said steel plate between said openings, a cantilever beam positioned in substantially parallel relationship above said steel plate and spaced therefrom, two aligned spaced apart openings in said cantilever beam in axial alignment with the openings in said steel plate, the lower surface of said cantilever beam being in contact with the upper end of said upstanding pivot, a specimen disposed in two of the axially aligned openings in said steel plate and said cantilever beam, a hardened steel stud positioned in two of the other axially aligned openings in said steel plate and said cantilever beam, and a threaded nut in engagement with one end of said stud whereby the torquing of said threaded nut causes one end of said cantilever beam to rotate downward around said pivot and apply a tension force to the specimen positioned between the other end of said cantilever beam and said steel plate.

2. The metallurgical specimen tester defined in claim 1 wherein the lower surface of the threaded nut on the steel stud is convex for engaging a concave cavity in the upper surface of the cantilever beam to prevent the stud from being bent axially as the torquing load is applied.

3. The metallurgical specimen tester defined in claim 2 wherein the upper end of said pivot is rounded for engagement with a complementary rounded groove in the lower surface of said cantilever beam.

4. The metallurgical specimen tester defined in claim 3 wherein a strain gage is mounted on the lower surface of said cantilever beam substantially midway between the groove for receiving the pivot and the opening for receiving the steel stud, the signal from said strain gage being proportional to the load applied to the specimen.

5. The metallurgical specimen tester defined in claim 4 including a calibration link with a pair of strain gages mounted diametrically opposite one another on the surface thereof, said calibration link being the same dimensions as said specimen whereby the readings from the strain gage on said cantilever beam can be correlated with a recorder to indicate the stress being applied to the specimen.

* * * * *